United States Patent [19]

Rutledge

[11] 4,085,124

[45] Apr. 18, 1978

[54] OXIDATIVE COUPLING OF ALKYLPHENOLS, ALKOXYPHENOLS AND 1-NAPHTHOLS CATALYZED BY METAL COMPLEXES OF AMINO COMPOUNDS

[75] Inventor: Thomas F. Rutledge, Wilmington, Del.

[73] Assignee: ICI Americas Inc., Wilmington, Del.

[21] Appl. No.: 634,644

[22] Filed: Nov. 24, 1975

[51] Int. Cl.$^2$ .................. C07C 37/00; C07C 45/16; C07C 49/62; C07C 49/72

[52] U.S. Cl. .................. 260/396 N; 260/47 ET; 260/613 A; 260/613 R; 260/619 B; 260/619 F; 260/620

[58] Field of Search ............ 260/396 N, 620, 619 B, 260/619 F, 613 A, 613 R, 47 ET

[56] References Cited

U.S. PATENT DOCUMENTS

| | | |
|---|---|---|
| 3,219,625 | 11/1965 | Blanchard et al. .............. 260/396 N |
| 3,219,626 | 11/1965 | Blanchard et al. .............. 260/396 N |
| 3,306,874 | 2/1967 | Hay .............................. 260/396 N |
| 3,306,875 | 2/1967 | Hay .............................. 260/396 N |

*Primary Examiner*—Vivian Garner
*Attorney, Agent, or Firm*—H. Jolyon Lammers

[57] ABSTRACT

Carbon-carbon coupled self-condensation products obtained by the oxidative coupling of alkylphenols, alkoxyphenols or 1-naphthols are prepared by contacting an aqueous mixture of the phenol or naphthol with oxygen in the presence of sufficient alkaline material to sustain a pH in the range of 5–10 during the oxidative coupling reaction and a catalyst system comprising a cupric, cobaltous, manganous or ferric complex of an aliphatic hydroxy amine,
a heterocyclic hydroxy amine,
a heterocyclic polyamine or,
an aliphatic diamine The mixture may optionally contain a surfactant.

17 Claims, No Drawings

OXIDATIVE COUPLING OF ALKYLPHENOLS, ALKOXYPHENOLS AND 1-NAPHTHOLS CATALYZED BY METAL COMPLEXES OF AMINO COMPOUNDS

FIELD OF THE INVENTION

The present invention relates generally to an improved process for preparing self-condensation products, such as diphenoquinones, biphenols, dinaphthenoquinones and binaphthols from alkylphenols, alkoxyphenols and naphthols and to a catalyst composition for use in said process. More particularly, the invention relates to a method of preparing carbon-carbon coupled condensation products of alkylphenols, alkoxyphenols or 1-naphthols by contacting an aqueous mixture of the phenol or naphthol with oxygen or an oxygen-containing gas optionally in the presence of a surfactant and sufficient alkaline material to sustain a pH in the range of 5–10 during the oxidative coupling reaction and a catalyst system comprising a cupric, manganous or ferric complex of an aliphatic hydroxy amine,
a heterocyclic hydroxy amine,
a heterocyclic polyamine or
an aliphatic diamine

DESCRIPTION OF THE PRIOR ART

It is well known in the art that substituted phenols can be oxidized to yield self-condensation products, including diphenoquinones, biphenols and polyphenoxy ethers. The procedure employed in the preparation of these derivatives is generally referred to as the oxidative coupling of phenols.

The self-condensation products resulting from these oxidative coupling reactions can be categorized as either the result of carbon-carbon coupling or carbon-oxygen coupling of said phenols. Diphenoquinones and biphenols are prepared by carbon-carbon coupling in accordance with the following general reactions depending upon the reactive sites available in the phenol employed.

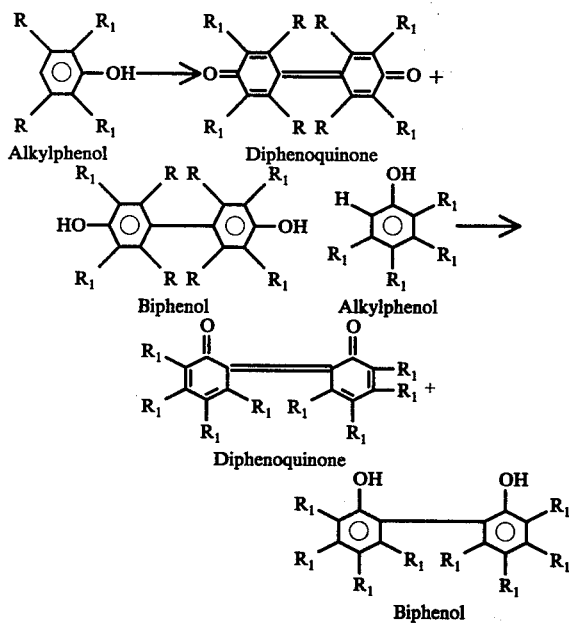

wherein R is hydrogen or $R_1$ and wherein $R_1$ is either alkyl, alkoxy, or another substituent all of which are well known in the art.

Similarly, polyphenoxy ethers are prepared by carbon-oxygen coupling in accordance with reactions such as the following general reaction:

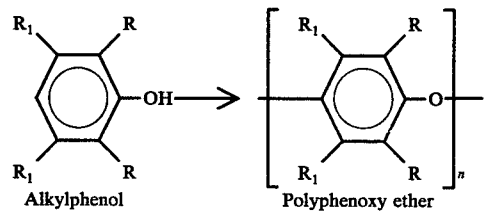

wherein R and $R_1$ are as defined above and $n$ is an integer.

A variety of materials, including metals and various salts and complexes thereof, have previously been disclosed as useful in promoting the oxidative coupling of alkylphenols. Thus, U.S. Pat. No. 2,785,188, discloses that copper powder may be utilized to prepare diphenoquinones from 2,6-dialkyl-4-halophenols. Similarly, various copper salts and combinations or complexes prepared from copper salts and a variety of nitrogen-containing compounds have been disclosed as useful in the preparation of both diphenoquinones and polyphenoxy ethers. These include, for example, cupric salts of primary and secondary amines (U.S. Pat. No. 3,306,874); and cupric salts of tertiary amines (U.S. Pat. No. 3,306,875 and U.S. Pat. No. 3,134,753). The use of cupric salts of carboxylic acids as the oxidizing agent in oxidative coupling reactions is also disclosed in the art. See, in the regard, U.S. Pat. No. 3,247,262.

The use of manganese amine chelates as oxidizing agents in oxidative coupling reactions is described in U.S. Pat. No. 3,825,521.

A variety of basic compounds have also been employed in oxidative coupling reactions. In many of these, such as those disclosed in U.S. Pat. No. 2,905,674, and in U.S. Pat. No. 2,785,188, the function of the alkaline material was to react with an acidic component, such as HCl, liberated during the course of the reaction and, therefore, a stoichiometric amount of the base was used.

It should be noted that, previous methods of preparing coupled products from alkyl- or alkoxy-phenols have required the use of either organic solvents or stoichiometric amounts of organic reagents. The present invention provides for a metal amine complex catalyst system useful in the preparation of carbon-carbon coupled phenols or naphthols in an aqueous reaction medium. Also, with most of the prior art systems the resulting product or products were determined by the particular catalyst employed and could not easily be controlled. The present invention provides for a system which can be readily modified to produce either the biphenol or diphenoquinone directly from the reaction mixture.

In accordance with the present invention, it has been found that "alkyl- or alkoxy- phenols" and "1-napthols" may be oxidatively coupled in a substantially basic aqueous medium if there is employed as a catalyst a system comprising a cupric, cobaltous, manganous or ferric complex of an "aliphatic hydroxy amine", a heterocyclic hydroxy amine,
a "heterocyclic polyamine" or
an "aliphatic diamine".

It has also been found that the type of product which is produced can be controlled by the amount of alkaline material and by the amount of catalyst employed in the catalyst system. By comparison, the prior art catalysts and processes employing said catalysts have a number of disadvantages which have restricted the utility of said catalyst and processes. These include (a) the requirement that the reaction be conducted in an organic solvent, (b) the fact that the primary product produced is often the polyphenoxy ether, and (c) the inability to form the biphenol, bisphenol or binaphthol derivative directly and in substantial quantities without requiring that this material be produced by a subsequent hydrogenation of the diphenoquinone, stilbenequinone or dinaphthenoquinone prepared in the oxidative coupling reaction. These disadvantages have been overcome by the use of the catalyst and process of the present invention as is described in detail hereinafter.

SUMMARY OF THE INVENTION

In accordance with the present invention, condensation products such as diphenoquinones, stilbenequinones, bisphenols, biphenols, dinaphthenoquinones and binaphthols are selectively prepared by contacting a substantially basic aqueous mixture of an "alkylphenol", an "alkoxyphenol" or a "1-naphthol" with oxygen or an oxygen-containing gas in the presence of a catalyst composition comprising a cupric, cobaltous, manganous or ferric complex of
an "aliphatic hydroxy amine",
a heterocyclic hyroxy amine,
a "heterocyclic polyamine" or
an "aliphatic diamine".

In a preferred embodiment the aqueous mixtures additionally contains a surfactant. The phenols or naphthols, metal complexes, and alkaline materials which may be utilized are critical to the present invention and are described in detail below.

PHENOLS/NAPHTHOLS

The phenols which may be employed in carrying out the present invention include both alkylphenols and alkoxyphenols. Specific phenols which may be utilized are described in detail below.

The alkylphenols which may be utilized are defined as any alkylphenol having at least two alkyl substituents, with the proviso that the phenols which have only two alkyl substituents must have the substituents in the ortho, ortho(2,6 in the formula below) or ortho, para (2,4 in the formula below) positions. These phenols are frequently referred to by the position of the alkyl substituent or substituents on the benzene ring as set forth in the following formula:

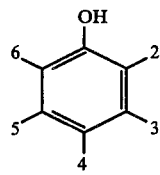

The process of the invention is applicable to any alkyl phenol having at least two alkyl substituents and steric properties such as to permit a coupling reaction. Thus if the para position is substituted with an alkyl group other than a methyl group, at least one ortho position must be unsubstituted. If one ortho and the para position are substituted, at least one of those substitutions must be a tertiary alkyl group. If both ortho positions are substituted, the para position must be either unsubstituted or substituted with a methyl group and no more than one meta position may be substituted with a tertiary alkyl group.

Thus, the alkylphenols will have one of the following formulas:

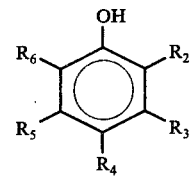

wherein $R_2$ and $R_6$ are alkyl and $R_3$, and $R_5$ are hydrogen or alkyl, and $R_4$ is hydrogen or methyl with the proviso that $R_3$ and $R_5$ cannot both be tertiary alkyl.

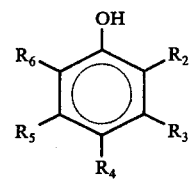

wherein $R_2$ and $R_4$ are alkyl provided that at least one of said alkyl groups is a tertiary alkyl and $R_3$ and $R_5$ are hydrogen or alkyl and $R_6$ is hydrogen.

As used herein, the term alkyl refers to any monovalent radical derived from a saturated aliphatic hydrocarbon by removal of one hydrogen atom therefrom. The term includes both straight chain and branched chain materials containing from 1 to about 12 carbon atoms. Preferred results are achieved with alkylphenols wherein the alkyl substituent contains from 1 to about 5 carbon atoms.

The alkyl substituents are referred to herein as primary, secondary or tertiary alkyl depending upon the greatest number of carbon atoms attached to any single carbon atom in the chain.

Condensation products of any alkylphenol coming within the above-mentioned definition may be prepared in accordance with the present invention. As is apparent from that definition, the alkylphenols include dialkylphenols, trialkylphenols, and tetraalkylphenols. Specifically, the phenols which may be utilized include the following:

Ortho, para-substituted phenols including 2,4-dialkylphenols, 2,3,4 trialkylphenols, 2,4,5 trialkylphenols, and 2,3,4,5-tetraalkylphenols wherein the alkyl groups are either methyl or a primary, secondary, or tertiary alkyl provided that at least one of the alkyl groups is either the 2 or the 4 position is a tertiary alkyl, and ortho, ortho-substituted phenols including 2,6-dialkylphenols, 2,3,6-trialkylphenols and 2,3,5,6-tetraalkylphenols wherein the alkyl groups are either methyl or a primary, secondary, or tertiary alkyl provided that in the case of 2,3,5,6-tetraalkylphenols at least one of the alkyl groups in either the 3 or the 5 position is either a primary or secondary alkyl.

Representative ortho, para-substituted phenols which may be used include, for example, 2,4-ditertiary-butylphenol, 2-methyl-4-tertiary-butylphenol, 2-tertiary-butyl-4-methylphenol, 2,4-ditertiary-amylphenol, 2,4-ditertiary-hexylphenol, 2-isopropyl-4-tertiary-butylphenol, 2-secondary-butyl-4-tertiary-butylphenol, 2-tertiary-butyl-3-ethyl-4-methylphenol, 2,5-dimethyl-4-tertiary-butylphenol, and 2-methyl-3-ethyl-4-tertiary-butylphenol.

Representative 2,6-dialkylphenols (ortho, ortho-substituted) include, for example, 2,6-xylenol, 2-methyl-6-butyl phenol, 2,6-diisobutylphenol, 2-octyl-6-methylphenol, 2-isobutyl-6-dodecylphenol, 2,6-ditertiary-butylphenol, 2,6-ditertiary-hexylphenol, 2-ethyl-6-methylphenol, 2-methyl-6-tertiary-butylphenol, 2,6-diisopropylphenol, 2,6-di-secondary-butylphenol, and 2-cyclohexyl-6-methylphenol.

Representative 2,3,6-trialkylphenols which may be utilized in accordance with the present invention include, for example, 2,3,6-trimethylphenol, 2,3,6-triethylphenol, 2,6-dimethyl-3-ethylphenol, 2,3-diethyl-6-tertiary-butylphenol, and 2,6-ditertiarybutyl-3-methylphenol.

Representative 2,3,5,6-tetraalkylphenols which may be utilized in accordance with the present invention include, for example, 2,3,5,6-tetramethylphenol, 2,3,5-trimethyl-6-tertiarybutylphenol, 2,6-ditertiary-butyl-3,5-dimethylphenol, 2,3,6-trimethyl-5-tertiary-butylphenol, 2,3-dimethyl-5,6-diethylphenol, and 2-methyl-3-ethyl-5-isopropyl-6-butylphenol.

When an ortho, para substituted alkylphenol is employed the coupling reaction proceeds in accordance with the following reaction resulting in the o, o'-coupled product.

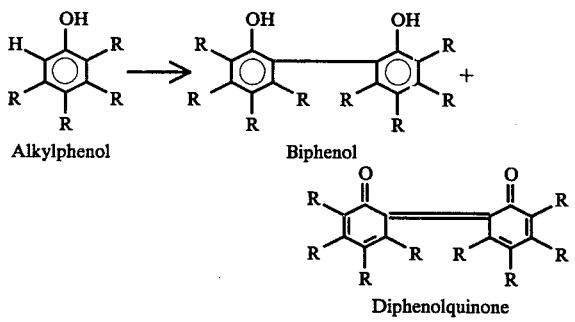

In this reaction each R represents hydrogen or an alkyl group as defined above depending upon whether di, tri, or tetra substituted alkylphenol is utilized.

Similarly, with the ortho, ortho-substituted alkylphenols, the reaction results in the p,p'-coupled product in accordance with the following reaction wherein R is hydrogen or alkyl depending upon which of the above-mentioned alkylphenols is used as the starting material.

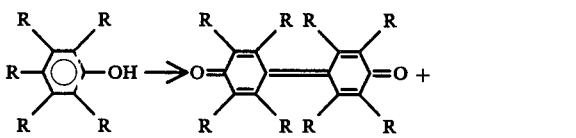

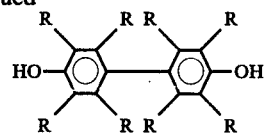

It has also been found that alkoxyphenols may be oxidatively coupled in accordance with the present invention. These include among others 2,6-disubstituted phenols wherein at least one of the substituents is an alkoxy group containing up to about six carbon atoms such as methoxy, ethoxy, propoxy, butoxy and pentoxy. In addition to the 2,6-dialkoxyphenols, 2-alkyl-6-alkoxyphenols, wherein the alkyl groups are as defined above for the alkylphenols, may be utilized. As used herein the term alkoxyphenols is intended to include both types of compounds. These compounds may be represented by the following general formulas:

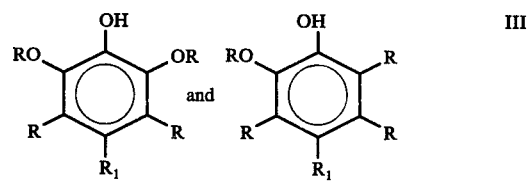

wherein each R is any alkyl group as defined above for the alkylphenols or OR and $R_1$ is either hydrogen or methyl, provided that the substituents adjacent to $R_1$ cannot both be tertiary alkyl or tertiary alkoxy. Representative alkoxyphenols which may be utilized include, for example, 2,6-dimethoxyphenol, 2,6-diethoxyphenol, 2,6-dibutoxyphenol, 2-methoxy-6-pentoxyphenol, 2-methyl-6-methoxyphenol and 2-ethyl-6-propoxyphenol, 2-methoxy-3-ethoxy-6-methylphenol.

When these phenols are utilized, the reaction proceeds in accordance with the following representative reaction resulting in the p,p'-coupled material.

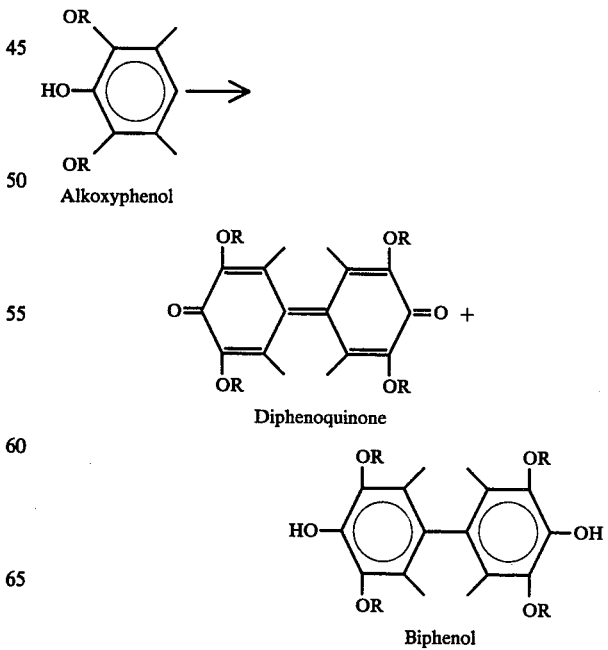

Mixtures of 2 different phenols may also be utilized. When this is done, there generally results a mixture of three different materials. Two of these are the products of the oxidative coupling of one molecule of one of the phenols with a second molecule in the same phenol. The third product is that resulting from the oxidative coupling of one molecule of the first phenol with one molecule of the second phenol. The products may be separated prior to use, as is well understood in the art.

Moreover, 1-naphthol and substituted 1-naphthols having at least 1 unsubstituted position ortho or para to the hydroxyl group may also be employed. The naphthols which may be coupled in accordance with the present invention are represented by the following general formula:

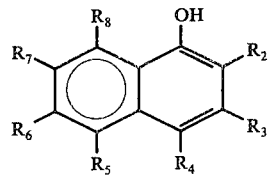

wherein $R_2$, $R_3$ and $R_4$ are hydrogen, alkyl containing from 1 to 5 carbon atoms, or alkoxy containing from 1 to 6 carbon atoms, provided that either or both $R_2$ or $R_4$ are hydrogen and $R_5$, $R_6$, $R_7$, and $R_8$ are hydrogen, alkyl containing from 1 to 5 carbon atoms or alkoxy containing from 1 to 6 carbon atoms provided that tertiary alkyl or tertiary alkoxy groups may not be attached to adjacent carbon atoms of the naphthalene molecule.

Representative naphthols which may be utilized include, for example, 1-naphthol, 2-methyl-1-naphthol, 2,3-dimethyl-1-naphthol, 4-ethyl-1-naphthol, and 2-methoxy-1-naphthol.

When a naphthol is employed, the coupling reaction takes place in accordance with the following general reactions depending upon the reactive positions — i.e., those either ortho or para to the hydroxy group — available. Thus, if $R_2$ is hydrogen and $R_4$ is alkyl or alkoxy, the reaction is as follows.

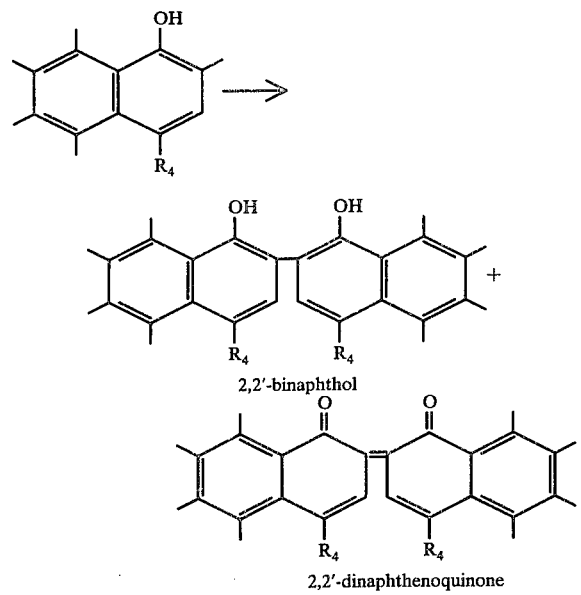

Similarly, if $R_4$ is hydrogen and $R_2$ is alkyl or alkoxy, the products are the 4,4'-binaphthol and the 4,4'-dinaphthenoquinone. When both $R_2$ and $R_4$ are hydrogen the products may be a mixture of the 2,2'-; 2,4'- and 4,4'-binaphthols and dinaphthenoquinones.

Finally, the catalyst system of this invention may also be employed to prepare coupled products of alkylphenols wherein all of the positions ortho and para to the hydroxy group are substituted and the substituent para to the hydroxy group is methyl. These alkylphenols may be represented by the following general formula:

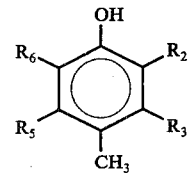

wherein $R_3$ is hydrogen, a primary, secondary or tertiary alkyl or an alkoxy group:

$R_5$ is a primary or secondary alkyl group containing from 1–5 carbon atoms and $R_2$ and $R_6$ are a primary, secondary or tertiary alkyl or an alkoxy group.

Representative compounds which may be employed include, for example, 2,4,6-trimethylphenol; 2,6-di-secondary-butyl-4-methylphenol; 2-methyl-6-t-butyl-4-methylphenol; and 2,3,4,6-tetramethylphenol.

When one of these alkylphenols is employed, the reaction proceeds in accordance with the following general reaction to produce the stilbenequinone or bisphenol derivative. These materials are useful in the same applications set forth above for the diphenoquinones, dinaphthenoquinones, biphenols and binaphthols.

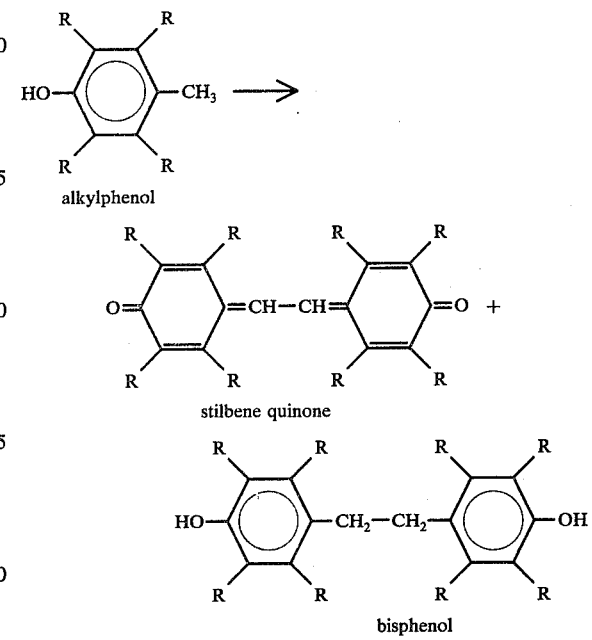

where the values for R are those specified in formula V.

It should be specifically noted that the term "alkyl phenol" is hereby defined as only those alkyl phenols of formulas I, II, and V and their isomers, the term "alkoxy phenol" is hereby defined as only those alkoxy phenols of formula III and their isomers and that the term "1-naphthol" is defined as only those 1-naphthols of formula IV and their isomers.

METAL COMPLEX

One of the essential components of the catalyst system of the present invention is a metal amine complex. As mentioned hereinbefore the metal source for this complex is a cupric, manganous, cobaltous or ferric ion which is complexed with certain amine compounds.

The amine compounds which may be complexed with the metal ion source useful in achieving the improved results of the present invention are selected from the group consisting of an aliphatic hydroxy amine, a heterocyclic hydroxy amine, a heterocyclic polyamine and an aliphatic diamine.

The term "aliphatic hydroxy amine" is hereby defined to include only those "aliphatic hydroxy amines" which may be primary, secondary or tertiary amines in which the groups attached to the nitrogen are either hydroxy aliphatic or hydroxy alkoxy or where one but not all of the groups may be alkyl. The hydroxy alkyl groups should not contain more than about 10 carbon atoms and the hydroxyl group should not be separated from the amino group by more than more than about 6 carbon atoms optionally interspersed with oxygen atoms. The hydroxy alkoxy groups may be mono, di- or trialkoxy and may contain more than 1 hydroxyl group. Specific hydroxy aliphatic amines include ethanolamine, propanolamine, isopropanol amine, 1-amino-5-hydroxypentane, diglycolamine, N-methylethanolamine, diethanolamine and triethanolamine.

Heterocyclic hydroxy amines useful in forming the metal complex include hydroxypyridines, hydroxyalkylpyridines, hydroxypiperidines, N-hydroxyalkoxypiperidines, hydroxypiperazines, hydroxyalkylpiperazines, hydroxyalkoxypiperazines and hydroxyaminoalkylpiperazines. Specific preferred heterocyclic hydroxy amines include 2-(2-hydroxyethyl)pyridine. Piperazines which show great effectiveness in forming the metal complex include N-(beta-hydroxyethyl)piperazine.

Certain heterocyclic polyamines are also useful in forming the metal complex of the catalyst system. The term "heterocyclic polyamines" is hereby defined to include only those wherein the one amino group is a primary alkyl amino group and another amino group can in addition be secondary if part of a cyclic system. Preferably the primary alkyl amine group is separated from one of the other amine groups by no more than 4 carbon atoms. Such compounds include histamines (4-imidazolylethylamine) and N-(beta-aminoethyl)piperazine.

The fourth group of amines is the aliphatic diamines. By aliphatic diamines is meant only those aliphatic diamines which have at least one primary amine group separated from the second amine group which can be primary or secondary, by no more than about 4 carbon atoms, optionally interspaced by oxygen or nitrogen atoms. Specific diamines useful in the present invention include ethylenediamine and 1,3-propanediamine.

In accordance with the invention the amine is complexed with a source of cupric, manganous, cobaltous or ferric ion. These ions may be derived from the corresponding metal salts and may include any of the following:

halides, such as chloride, bromide and iodide, basic halo hydroxides such as represented by the formula $CuX_2 \cdot Cu(OH)_2$ or $CoX_2 \cdot Co(OH)_2$ wherein X is chlorine, fluorine, bromine, or iodine, carboxylates, such as acetate, benzoate, and butyrate nitrates sulfates alkyl sulfates wherein the alkyl group is either a straight or branched chain alkyl containing from 1 to about 20 carbon atoms including, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl, aryl sulfonates wherein the aryl group contains at least one aromatic ring which may, if desired, have alkyl substituents such as those mentioned above, attached thereto including, for example, benzene, naphthalene, dodecyl benzene, and methyl naphthalene.

carbonates, basic carbonate — i.e., $CuCO_3 \cdot Cu(OH)_2, 2CoCO_3 \cdot Co(OH)_2 \cdot H_2O$ hydroxides, chlorates — i.e., $Cu(ClO_3)_2$, If either metal nitrate or metal sulfate is employed as the metal source, these materials may be prepared in situ in the reaction medium by adding thereto a material, such as cupric nitrite or cobaltous sulfite, which is oxidized to the desired nitrate or sulfate in the reaction vessel.

Also, if a metal alkyl sulfate wherein the alkyl group contains at least 8 carbon atoms is employed, this material may function both as the metal ion source and the optional surfactant and it is, therefore, not usual to include a separate additional surfactant in the catalyst system.

These complexes may be prepared in any manner and the preparation thereof has not been found to be critical to the present invention. Similarly the ratio of amine to metal source has been found to be not narrowly critical. It should be noted that if the ratio of amine to metal source is less than one, less complex is formed. The following three methods have been employed but other methods which will be readily apparent to those skilled in the art from the description of the invention given herein, may also be utilized.

First, suitable amounts of the amine and a source of cupric, cobaltous or ferric ions may be combined in a suitable medium such as water and reacted to form the complex. The complex is prepared by simply stirring the solution for a period of time. If desired, heat may be applied to accelerate formation of the complex.

Alternatively, the amine and the source of the metal ion may simply be combined and added to the reaction mixture wherein the complex of the amine is formed. When this is done, any basic compound required to neutralize acidic by-products of the complex forming reaction is also added directly to the reaction mixture.

Finally, the amine, the source of metal ion, and any required basic compound may be added separately to the reaction medium and the complex formed in situ. As mentioned above, the method by which the metal complex is prepared has not been found to be critical to the present invention. However, further improved conversion results have been achieved when the source of metal ion and the amine are combined prior to addition to the reaction medium.

The amount of metal complex employed has not been found to be narrowly critical to the process of the present invention. However, it is preferred to employ at least 0.02 mmols of the complex per 100 mmols of alkylphenol. If less than this amount is used the reaction is slower and the yields are low. Similarly, the maximum amount of complex employed is not generally greater than 1 mmol of the complex per 100 mmol of alkylphenol. At amounts much in excess of this the cost of the catalyst results in an uneconomic system.

Although any of the above-mentioned metal complexes may be used, improved conversion results have been achieved with the cupric complexes of ethanolamine.

As mentioned above, an advantage of the catalyst system and of the process of the present invention is that the reaction can be carried out in an aqueous medium instead of an organic solvent as has been used in prior art systems. However, it has not been found to be critical to the present invention to employ a water soluble metal complex. Thus, materials which are insoluble in water as well as those which are soluble may be utilized.

Surfactant

The catalyst composition of the present invention may also include, as an optional component thereof, a surfactant. The presence of a surfactant moderately improves conversion results and additionally allows easier cleaning of large reactors. A variety of surfactants also known as dispersants, are well known in the art and, as used herein, the term surfactant is intended to refer to organic compounds that contain in the molecule both hydrophobic and hydrophilic groups.

Surfactants are often classified, based on the hydrophilic (water liking)group which they contain, as either anionic, cationic, nonionic, or amphoteric. Any such surfactants may be employed in the present invention.

Surfactants are discussed in detail in the *Encyclopedia of Chemical Technology*, Kirk-Othmer, Second Edition Vol. 19 at pages 508–589, and any of the surfactants described therein may be utilized in the present invention.

The amount of surfactant employed has not been found to be critical to the utility of the catalyst system in carrying out the improved process of the present invention. However, if the use of a surfactant is desirable such as for example to increase the amount of carbon-carbon coupled product, there should be included in the reaction mixture at least about 0.2 mmols of surfactant per 400 mmol of phenol or naphthol. Preferred conversion results are achieved when the amount of surfactant employed is equal to from about 0.2 to about 0.6 mmols of surfactant per 400 mmol of phenol or naphthol. Additional amounts of the surfactant may be employed; however, the use of greater amounts of surfactant has usually not been found to significantly increase the total yield of product and it is, therefore, not generally desirable to include additional material in the reaction mixture. When a cupric alkyl sulfate as defined above is employed, both as the metal in source and as the surfactant, the amount of said material employed is preferably equal to at least 0.2 mmols per 400 mmol of phenol or naphthol — i.e., the preferred amount of metal compound plus the preferred amount of surfactant.

Alkaline Material

In accordance with the present invention, an alkaline material is also included in the catalyst composition to ensure that the pH during the reaction is maintained in the range of 5–10. It has been found that the use of an alkaline material to raise the pH in the present system increases the conversion to carbon-carbon coupled products and decreases the conversion to carbon-oxygen coupled products. The use of such a material to maintain the required pH also increases the rate of the oxidative coupling reaction and decreases the amount of the metal compound which must be utilized.

The alkaline material useful in achieving the pH of the reaction and the improved results of the present invention is selected from the group consisting of alkali metal hydroxides, alkali metal carbonates, and alkali metal bicarbonates. The alkaline material may be added either as a single compound or as a mixture of compounds. Representative materials which may be employed include, for example, sodium hydroxide, potassium hydroxide, lithium hydroxide, sodium carbonate, lithium carbonate, sodium bicarbonate, rubidium carbonate, rubidium hydroxide, cesium bicarbonate, and cesium hydroxide.

The amount of alkaline material employed has not been found to be narrowly critical to the present invention as long as the required pH range is maintained. However, preferred results are achieved when the amount of said material is equal to at least about 3 millimols per mol of phenol or naphthol. Smaller amounts of alkaline material will normally result in a reaction pH of less than 5 and will normally cause a low molar conversion of starting compound to final product. A preferred pH range is from about 8 to 9. Increased amounts of alkaline material may also be utilized in carrying out the present invention. It has been found that, for a given set of reaction conditions, increasing the amount of alkaline material increases the total conversion to carbon-carbon coupled products and the relative amount of diphenoquinone, stilbenequinone, or dinaphthenoquinone as compared to the amount of diphenol, bisphenol or binaphthol. Thus, by varying the amount of alkaline material to vary the pH within the required pH range of 5–10, the type of product can be controlled.

Besides the selective production of carbon-carbon coupled products, an additional advantage of the catalyst system of the present invention is the ability to control the type of carbon/carbon coupled product produced. Thus, it is possible to prepare selectively either diphenoquinone or biphenol, stilbenequinone, or bisphenol, or dinaphthenoquinone or binaphthol, in accordance with the present invention. This result is achieved by controlling the amount of alkaline material included in the system. Generally, as the amount of alkaline material is increased, the percentage of quinone derivative produced also increases. Therefore to obtain larger amounts of biphenolic product as opposed to quinone derivatives it is desirable to use sufficient alkaline material to raise the pH of the reaction material to a range of about 5–9, preferably 7.5–8.5. Higher pH values resulted in significant levels of oligomer formation. (carbon-oxygen coupled products.)

Reaction Conditions

As mentioned above, an advantage of the catalyst system and process of the present invention is that it makes it possible for the oxidative coupling reaction to be carried out in an aqueous medium. The amount of water employed has not been found to be critical to the present invention and any amount of water which will permit the reaction mixture to be stirred during the course of the reaction may be employed. It should also be noted again that it is not essential that the various components be soluble in water and the term aqueous mixture as used herein is intended to include solutions, slurries, suspensions and the like.

The components of the reaction mixture may be combined in any suitable manner. Thus, the phenol or naphthol, surfactant, metal complex, alkaline material and water may be combined in any order in a suitable reaction vessel. Alternatively, and in a preferred method, the phenol or naphthol and optionally the surfactant are combined in water in a suitable reaction vessel, the mixture is stirred rapidly, preferably by utilizing a stainless steel impeller turning at 3,000-10,000 RPM and an aqueous mixture of the metal salt compound is prepared to which the amine is added followed by an aqueous solution of the alkaline material. In modifications of this procedure the metal complex may be added prior to heating or the metal complex and alkaline material may particularly at low pH ranges be combined prior to addition to the reaction mixture.

The reaction mixture comprising phenol or naphthol, water, metal complex and alkaline material is contacted with a suitable oxidizing agent to convert the phenol or naphthol to the desired product. Oxidizing agents which may be employed in carrying out the present invention include oxygen either alone or as an oxygen-containing gas, such as air. The oxygen may be introduced into the reaction mixture either directly as oxygen or as an oxygen-generating material such as ozone, hydrogen peroxide, or an organic peroxide. The amount of oxygen utilized should be sufficient to obtain the desired conversion of the phenol or naphthol to the coupled product. To assure that sufficient oxygen is present, oxygen should be introduced into the reaction mixture continuously during the course of the reaction.

The reaction conditions — i.e., time and temperature — employed have not been found to be narrowly critical to the process of the present invention. Preferred results have been achieved when the reaction mixture is maintained at from about 80° to 90° C. during the course of the reaction. However, temperatures above and below this preferred range may be utilized. At lower temperatures the reaction rate is reduced and at temperatures below about 40° C. it is so slow as to result in an uneconomic system. When operating at atmospheric pressure, as is desirable in some commercial operations, the practical upper limit on the temperature is 100° C., the boiling point of the water.

If the reaction is conducted at increased oxygen pressure, the reaction time is decreased, the total yield of coupled product is usually increased, and the relative amount of quinone derivative is also usually increased.

The amount of time required for completion of the reaction depends on the temperature employed and other variables such as the pressure, concentration of phenol or naphthol and the amount of metal complex, surfactant if present, and alkaline material employed. However, it has been found that, when conducted at atmospheric pressure, the reaction is usually completed in 6 hours or less.

Although, as mentioned above, the process of the present invention results primarily in the production of carbon-carbon coupled products, there are also sometimes included in the solids removed from the reaction mixture the following: (a) unreacted phenol or naphthol, and (b) low molecular weight polyphenoxy ether. The polyphenoxy ether and phenol or naphthol may be removed by washing the solids with a solvent in which these materials are soluble, such as an aromatic hydrocarbon — e.g., toluene, benzene, or a halogenated solvent — e.g., methylene chloride. If it is desired to separate the materials from each other and from the solvent, this may be done by distillation.

If the reaction results in the mixture of biphenol and diphenoquinone, bisphenol and stilbene quinone, or binaphthol and dinaphthenoquinone, these materials may be separated by any method known in the art. An especially convenient way of separating the materials is to stir the solid product with a dilute aqueous solution of sodium hydroxide, which converts the biphenol, bisphenol or binaphthol to the sodium salt which is usually soluble in water. The insoluble diphenoquinone, stilbene quinone or dinaphthenoquinone may then be filtered off and the biphenol, bisphenol or binaphthol recovered by adding the aqueous solution of the sodium salt thereof to a dilute solution of a strong acid such as hydrochloric acid from which the biphenol, bisphenol or binapthol precipitates. Alternatively, the entire product may be hydrogenated or chemically reduced and converted to only the biphenol, bisphenol or binaphthol.

The diphenoquinones and/or biphenols as well as the binaphthols, bisphenols and dinaphthenoquinones and stilbene quinones produced in accordance with the present invention are suitable for any of the uses of these materials which have heretofore been described in the art. Thus, the diphenoquinones and dinaphthenoquinones may be used as inhibitors of oxidation, peroxidation, polymerization and gum formation in gasolines, aldehydes, fatty oils, lubricating oils, ethers and similar compounds as mentioned in U.S. Pat. No. 2,905,674 issued to Filbey. The diphenoquinones may also be hydrogenated, employing conventional techniques, to yield the corresponding biphenol. The biphenols may be employed as stabilizers in gasoline and other petroleum products as described in U.S. Pat. No. 2,479,948 issued to Luten et al.

In order to describe the present invention so it may be more clearly understood the following examples are set forth. These examples are given primarily for the purpose of illustration and any enumeration of detail contained therein should not be interpreted as a limitation on the concept of the present invention.

EXAMPLE I

Into a first flask there were added:
 0.4 grams (2 mmols) of cupric acetate $Cu(OAc)_2 \cdot H_2O$,
 0.24 grams (4 mmols) of ethanolamine
 25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 0.2 gm of sodium lauryl sulfate, 150 grams of deionized water and 48.8 grams (400 mmols) of 2,6-xylenoyl.

To the resulting slurry which was stirred using a Labline cruciform stainless steel impeller turning at about 6,000 rpm there was added the stirred copper amine complex solution prepared above. The resulting mixture was stirred for 15 minutes after which 0.672 gms of sodium bicarbonate (as a 8 ml of 1.0 N) solution was added over a period of 3 minutes. At this point the pH of the mixture was found to be 8.7. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 4.7. A sample of the solid was removed, dissolved in acetone and analyzed by gas-liquid chromatography. The analysis indicated that 3.7 mmol percent of the 2,6-xylenol was unreacted.

The solid product was then washed with xylene to remove oligomer and dried at 60° C. overnight. 34.7 gm of product was obtained as a yellow solid which contained 0.27% diphenoquinone and 99.9% tetramethylbiphenol as determined by spectrophotometric analysis.

EXAMPLE 2

Into a first flask there were added:
  0.4 grams (2 mmols) of cupric acetate $Cu(OAc)_2 \cdot H_2O$,
  0.34 grams (5.6 mmols) of ethanolamine,
  25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 150 grams of deionized water and 48.8 grams (400 mmols) of 2,6-xylenol.

To the resulting slurry which was stirred using a Labline cruciform stainless steel impeller turning at about 6,000 rpm there was added the stirred copper amine complex solution prepared above. The resulting mixture was stirred for 15 minutes after which 0.672 gms of sodium bicarbonate (as a 8 ml of 1.0 N) solution was added over a period of 3 minutes. At this point the pH of the mixture was found to be 8.4. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 5.7. A sample of the solid was removed, dissolved in acetone and analyzed by gas-liquid chromatography. The analysis indicated that 6 mol percent of the 2,6-xylenol was unreacted.

The solid product was then washed with xylene to remove oligomer and dried at 60° C. overnight. 30.4 gm. product was obtained as a yellow solid which contained 0.88% diphenoquinone and 99% tetramethylbiphenol as determined by spectrophotometric analysis.

EXAMPLE 3

Into a first flask there were added;
  0.4 grams (2 mmols) of cupric acetate $Cu(OAc)_2 \cdot H_2O$,
  0.67 grams (11.1 mmols) of ethanolamine,
  25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 150 grams of deionized water and 48.8 grams (400 mmols) of 2,6-xylenol.

To the resulting slurry which was stirred using a Labline cruciform stainless steel impeller turning at about 6,000 rpm there was added the stirred copper amine complex solution prepared above. The resulting mixture was stirred for 15 minutes after which 1.008 gms of sodium bicarbonate (as 12 ml of 1.0 N) solution was added over a period of 3 minutes. At this point the pH of the mixture was found to be 9.3. The sample was returned to the reactor which was then heated to 80° C. The mixture was stirred under oxygen. The oxygen flow was rapid at the beginning to flush the system. After about ½ hours, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the presecribed reaction time of 6 hours.

PRODUCT ISOLATION

The reaction slurry was cooled to room temperature and filtered to remove the water phase, washed once with 200 ml with water. The water phase had a pH of 7.7. A sample of the solid was removed, dissolved in acetone and analyzed by gas-liquid chromatography. The analysis indicated that 3.7 mol percent of the 2,6-xylenol was unreacted.

The solid product was then washed with xylene to remove oligomer and dried at 60° C. overnight. 27.5g of the product was obtained as a yellow solid which contained 4.85% diphenoquinone and 51.5% tetramethylbiphenol as determined by spectrophotometric analysis.

EXAMPLE 4

Into a first flask there were added;
  0.4 grams (2 mmols) of cupric acetate $Cu(OAc)_2 \cdot H_2O$,
  0.32 grams (4 mmols) of 4-amino-1-butanol,
  25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 150 grams of deionized water and 48.8 grams (400 mmols) of 2,6-xylenol.

To the resulting slurry which was stirred using a Labline cruciform stainless steel impeller turning at about 6,000 rpm there was added the stirred copper amine complex solution prepared above. The resulting mixture was stirred for 15 minutes after which 0.672 gms of sodium bicarbonate (as 8 ml of 1.0 N) solution was added over a period of 3 minutes. At this point the pH of the mixture was found to be 9.1. The sample was returned to the reactor which was then heated to 80° C. The mixture was stirred under oxgyen. The oxgyen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxgyen for the prescribed reaction time of 6 hours.

PRODUCT ISOLATION

The reaction slurry was cooled to room temperature and filtered to remove the water phase, washed once with 200 ml with water. The water phase had a pH of 6.9. A sample of the solid was removed, dissolved in acetone and analyzed by gas-liquid chromatography. The analysis indicated that 5.0 mol percent of the 2,6-xylenol was unreacted.

The solid product was then washed with xylene to remove oligomer and dried at 60° C. overnight. 31.0 gm. of product was obtained as a yellow solid which contained 11.8% diphenoquinone and 88.2% tetramethylbiphenol was determined by spectrophotometric analysis.

EXAMPLE 5

Into a first flask there were added;
0.4 grams (2 mmols) of cupric acetate Cu(OAc)$_2$.H$_2$O,
0.30 grams (4 mmols) of 2-amino-1-propanol,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 150 grams of deionized water and 48.8 grams (400 mmols) of 2,6-xylenol.

To the resulting slurry which was stirred using a Labline cruciform stainless steel impeller turning at about 6,000 rpm there was added the stirred copper amine complex solution prepared above. The resulting mixture was stirred for 15 minutes after which 0.672 gms of sodium bicarbonate (as 8 ml of 1.0 N) solution was added over a period of 3 minutes. At this point the pH of the mixture was found to be 8.2. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 5.4. A sample of the solid was removed, dissolved in acetone and analyzed by gas-liquid chromatography. The analysis indicated that 3.1 mol percent of the 2,6-xylenol was unreacted.

The solid product was then washed with xylene to remove oligomer and dried at 60° C. overnight. 30.8 gm of product was obtained as a yellow solid which contained no diphenoquinone and 99.+% tetramethylbiphenol as determined by spectrophotometric analysis.

EXAMPLE 6

Into a first flask there were added:
0.4 grams (2 mmols) of cupric acetate Cu(OAc)$_2$.H$_2$O,
0.30 grams (4 mmols) of N-methylethanolamine
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 150 grams of deionized water and 48.8 grams (400 mmols) of 2,6-xylenol.

To the resulting slurry which was stirred using a Labline cruciform stainless steel impeller turning at about 6,000 rpm there was added the stirred copper amine complex solution prepared above. The resulting mixture was stirred for 15 minutes after which 0.672 gms of sodium bicarbonate (as 8 ml of 1.0 N) solution was added over a period of 3 minutes. At this point the pH of the mixture was found to be 8.9. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 7.4. A sample of the solid was removed, dissolved in acetone and analyzed by gas-liquid chromatography. The analysis indicated that 26.3 mol percent of the 2,6-xylenol was unreacted.

The solid product was then washed with xylene to remove oligomer and dried at 60° C. overnight. 21.9 gm of product was obtained as a yellow solid which contained no diphenoquinone and 99.+% tetramethylbiphenol as determined by spectrophotometric analysis.

EXAMPLE 7

Into a first flask there were added;
0.4 grams (2 mmols) of cupric acetate Cu(OAc)$_2$.H$_2$O,
0.24 grams (4 mmols) of ethanolamine,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 0.2 gm of sodium lauryl sulfate, 150 grams of deionized water and 48.8 grams (400 mmols) of 2,6-xylenol.

To the resulting slurry which was stirred using a Labline cruciform stainless steel impeller turning at about 6,000 rpm there was added the stirred copper amine complex solution prepared above. The resulting mixture was stirred for 15 minutes after which 1.008 gms of sodium bicarbonate (as 12 ml of 1.0 N) solution was added over a period of 3 minutes. At this point the pH of the mixture was found to be 8.5. The sample was returned to the reactor which was then heated to 80° C. The mixture was stirred under oxygen. The oxygen flow was rapid at the beginning to flush the system. After about ½ hour, oxgyen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 8.5. A sample of the solid was removed, dissolved in acetone and analyzed by gas-liquid chromatography. The analysis indicated that 10.4 mol percent of the 2,6-xylenol was unreacted.

The solid product was then washed with xylene to remove oligomer and dried at 60° C. overnight. 26.0 gm of product was obtained as a yellow solid which contained no diphenoquinone and 99% tetramethylbiphenol as determined by spectrophotometric analysis.

EXAMPLE 8

Into a first flask there were added;
  0.4 grams (2 mmols) of cupric acetate $Cu(OAc)_2 \cdot H_2O$,
  0.476 grams (4 mmols) of 1-amino-3-(2-hydroxyethoxy) propanol
  25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 150 grams of deionized water and 48.8 grams (400 mmols) of 2,6-xylenol.

To the resulting slurry which was stirred using a Labline cruciform stainless steel impeller turning at about 6,000 rpm there was added with stirred copper amine complex solution prepared above. The resulting mixture was stirred for 15 minutes after which 0.672 gms of sodium bicarbonate (as 8 ml of 1.0 N) solution was added over a period of 3 minutes. At this point the pH of the mixture was found to be 8.7. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 5.5. A sample of the solid was removed, dissolved in acetone and analyzed by gas-liquid chromatography. The analysis indicated that 10.5 mol percent of the 2,6-xylenol was unreacted.

The solid product was then washed with xylene to remove oligomer and dried at 60° C. overnight. 20.2 gm of product was obtained as a yellow solid which contained no diphenoquinone and 99.+% tetramethylbiphenol as determined by spectrophotometric analysis.

EXAMPLE 9

Into a first flask there were added;
  0.4 grams (2 mmols) of cupric acetate $Cu(OAc)_2 \cdot H_2O$,
  0.42 grams (4 mmols) of diethanolamine,
  25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 150 grams of deionized water and 48.8 grams (400 mmols) of 2,6-xylenol.

To the resulting slurry which was stirred using a Labline cruciform stainless steel impeller turning at about 6,000 rpm there was added the stirred copper amine complex solution prepared above. The resulting mixture was stirred for 15 minutes after which 0.672 gms of sodium bicarbonate (as 8 ml of 1.0 N) solution was added over a period of 3 minutes. At this point the pH of the mixture was found to be 8.0. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 7.8. A sample of the solid was removed, dissolved in acetone and analyzed by gas-liquid chromatography. The analysis indicated that 99.+% mol percent of the 2,6-xylenol was converted.

The solid product was then washed with xylene to remove oligomer and dried at 60° C. overnight. The product contained 50% diphenoquinone and 50% tetramethylbiphenol as determined by spectrophotometric analysis.

EXAMPLE 10

Into a first flask there were added;
  0.4 grams (2 mmols) of cupric acetate $Cu(OAc)_2 \cdot H_2O$,
  0.59 grams (4 mmols) of triethanolamine,
  25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 150 grams of deionized water and 48.8 grams (400 mmols) of 2,6-xylenol.

To the resulting slurry which was stirred using a Labline cruciform stainless steel impeller turning at about 6,000 rpm there was added the stirred copper amine complex solution prepared above. The resulting mixture was stirred for 15 minutes after which 0.672 gms of sodium bicarbonate (as 8 ml of 1.0 N) solution was added over a period of 3 minutes. At this point the pH of the mixture was found to be 7.8. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 8.0. A sample of the solid was removed, dissolved in acetone and analyzed by gas-liquid chromatography. The analysis indicated that 30% mol percent of the 2,6-xylenol was unreacted.

The solid product was then washed with xylene to remove oligomer and dried at 60° C. overnight. The product contained 49.6% diphenoquinone and 50.4% tetramethylbiphenol as determined by spectrophotometric analysis.

EXAMPLE 11

Into a first flask there were added:
0.1 grams (0.5 mmols) of cupric acetate Cu-(OAc)$_2$.H$_2$O,
0.03 grams (0.5 mmols) of ethanolamine,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 225 grams of deionized water and 48.8 grams (400 mmols) of 2,6-xylenol.

To the resulting slurry which was stirred using a Labline cruciform stainless steel impeller turning at about 6,000 rpm there was added the stirred copper amine complex solution prepared above. The resulting mixture was stirred for 15 minutes after which 0.672 gms of sodium bicarbonate (as 8 ml of 1.0 N) solution was added over a period of 3 minutes. At this point the pH of the mixture was found to be 8.4. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 8.1. A sample of the solid was removed, dissolved in acetone and analyzed by gas-liquid chromatography. The analysis indicated that 11.3 mol percent of the 2,6-xylenol was unreacted.

The solid product was then washed with xylene to remove oligomer and dried at 60° C. overnight. 30.3 gm of product was obtained as a yellow solid which contained no diphenoquinone and 99.+% tetramethylbiphenol as determined by spectrophotometric analysis.

Examples 12, 13 and 14 were prepared according to the procedure of Example 11 differing only in the mole ratio of ethanolamine to cupric ion present and the pH maintained during the reaction. The results are shown in the following Table I.

Examples 15–18 and 50–54 were prepared to determine the effect of base. The Examples were prepared according to the general procedure of Example 12 differing only where indicated. Examples 50–54 were subjected to continuous pH maintenance. The results which indicate a buffer effect in Examples 15–18 are shown in the following Table 2.

To indicate the effect of varying concentrations of catalyst, examples 19, 20, 21, 22, 23 and 24 were prepared according to the Procedure of Example 12. Example 23 was prepared by the Procedure of Example 12 with the additional presence of 0.10 g of sodium lauryl sulfate surfactant dissolved in 175 ml of H$_2$O. The results are reported in the following Table 3.

The utility of several aliphatic diamines is demonstrated by the following examples 25, 26, 27, and 28. Example 29 utilizes a heterocyclic polyamine. Examples 25 to 29 were prepared according to the procedure of Example 12 with minor variations in the amount of amine and sodium bicarbonate. The results are reported in the following Table 4.

The utility of several heterocyclic hydroxy amines is demonstrated by Examples 30 to 38 which were prepared according to Example 12. The results are shown in Table 5.

The utility of different metals in the metal amine complex is demonstrated in examples 39 to 41.

TABLE I

| Example | Moles Ethanolamine:Cu$^{+2}$ | pHo | pHf | Mole % Conversion of 2,6-Xylenol | Oligo. | TMDQ | TMBP |
|---|---|---|---|---|---|---|---|
| 11 | 1 | 8.4 | 8.1 | 88.7 | 17.7 | 0 | 63.6 |
| 12 | 2 | 8.3 | 6.3 | 95.7 | 18.1 | 0 | 71.5 |
| 13 | 4 | 8.6 | 8.8 | 96.1 | 16.4 | 0 | 68.6 |
| 14 | 8 | 8.8 |  | 84.0 | 17.7 | 0 | 64.3 | perature was controlled by a Therm-O-Watch. The

TABLE II

| Examples | Base meq's | pHo | PHC$^3$ | PHf | SLS$^1$ g. | Mole % Conversion Of 2,6-xylenol | Oligo. | TMDQ | TMBP |
|---|---|---|---|---|---|---|---|---|---|
| 15 | 4 NaHCO$_3$ | 8.4 | — | 5.0 | — | 82.6 | 17.1 | — | 46.7 |
| 16 | 8 NaHCO$_3$ | 8.3 | — | 6.3 | — | 95.7 | 18.1 | — | 71.5 |
| 17 | 16 NaHCO$_3$ | 8.8 | — | 8.8 | — | 90.0 | 9.6 | — | 68.2 |
| 18 | 32 NaHCO$_3$ | 8.8 | — | 8.9 | — | 98.3 | 18.3 | 12.6 | 58.9 |
| 50 | 13 NaHCO$_3$ | — | 6 | — | 0.1 | 50 | 6.7 | — | 44.6 |
| 51$^4$ | 7 NaHCO$_3$ | — | 5 | — | 0.1 | 37.5 | — | — | 25 |
| 52$^4$ | 15.5 NaHCO$_3$ | — | 7.5 | | 0.1 | 99 | 15.6 | 4.2 | 77.5 |

TABLE II-continued

| Examples | Base meq's | pHo | PHC[3] | PHf | SLS[1] g. | Mole % Conversion Of 2,6-xylenol | Oligo. | TMDQ | TMBP |
|---|---|---|---|---|---|---|---|---|---|
| 53[4] | 35 NaHCO₃ | — | 8.5 | — | 0.1 | 99 | 14 | 1.6 | 74.1 |
| 54[4] | A[2] NaHCO₃ | — | 9.5 | — | 0.1 | 99 | — | 0.2 | 55.2 |

[1] SLS - sodium lauryl sulfate
[2] A - to maintain a pH of 9.5 there was added a total of:
  18 meq. of NaCO₃
  37 meq. of NaOH (1.0 N solution)
  109 meq of NaOh (solid 99% pure)
[3] pHC - controlled pH
[4] The reaction mixture of examples 50-54 were heated to 80° C. prior to the addition of alkaline material.

TABLE III

| Ex. | Mmoles[5] Catalyst | pHo | pHf | Mole % Conversion of 2,6-xylenol | To: Oligo | TMDQ | TMBP |
|---|---|---|---|---|---|---|---|
| 19 | 2 | 8.4 | 5.7 | 94 | 31.5 | 0.53 | 62 |
| 20 | 1 | 8.1 | 6.1 | 89.9 | 20.2 | 0 | 62 |
| 21 | 0.5 | 8.3 | 6.3 | 95.7 | 18.1 | 0 | 71.5 |
| 22 | 0.25 | 8.5 | 8.6 | 89.9 | 7.3 | 0 | 62.4 |
| 23 | 0.25 | 8.3 | 6.4 | 98+ | 6.8 | 0 | 79.8 |
| 24 | 0.10 | 8.3 | 9.4 | 81.6 | 29.9 | 0 | 51.7 |

[5] Relative concentration of ethanolamine to Cu is 2 to 1.

TABLE IV

| Example | Diamine | Mmoles | NaHCO₃ | pHo/pHf | Mole % Conv. 2,6- | Oligo. | TMDQ | TMBP |
|---|---|---|---|---|---|---|---|---|
| 25 | H₂N—CH₂CH₂—NH₂ | 4 | 8 | 8.8/8.5 | 95 | 35 | 26.3 | 33.8 |
| 26 | H₂N—CH₂CH₂—CH₂—NH₂ | 4 | 8 | 9.2/5.7 | 95.5 | 50.4 | 18.9 | 26.2 |
| 27 | H₂N—CH₂CH₂—NH₂ | 2 | 8 | 8.7/9.4 | 81.2 | 6 | 2.8 | 72.1 |
| 28 | H₂N—CH₂CH₂—NH₂ | 2 | 16 | 8.7/8.7 | — | 16 | 10.9 | 48.8 |
| 29 | L(+) Histamine 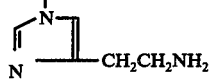 | 2 | 12 | 6.7/5.3 | 92.9 | 36.2 | 27.1 | 29.6 |

TABLE V

| Examples | Pyridine | Mmoles | Cu⁺² Amine | Mmoles NaHCO | pHo/pHf | Mole % Conv. 2,6- | Oligo. | Mole % Conv. to TMDQ | TMBP |
|---|---|---|---|---|---|---|---|---|---|
| 30 | 2-Hydroxypyridine | 4 | ½ | 8 | 7.1/6.0 | 67 | 18.6 | 0 | 48.4 |
| 31 | 3-Hydroxypyridine | 4 | ½ | 8 | 7.1/5.1 | — | — | 4 | 34.8 |
| 32 | ⟨N⟩—CH₂CH₂OH | 4 | ½ | 8 | 7.1/4.9 | 74.5 | 29.2 | 0 | 45.3 |

| Examples | Amine | Mmoles | Cu² Amine Ratio | Mmoles of NaHCO₃ pHo/pHf | Mole % Conv. 2,6- | Oligo. | Mole % Conv. to TMDQ | TMBP |
|---|---|---|---|---|---|---|---|---|
| 33 | 3-Hydroxy-piperidine | 4 | ½ | —/ | 55.7 | 21.7 | 0 | 34 |
| 34 | 4-Hydroxy-piperidine | 4 | ½ | 8.5/7.9 | 75 | 37.5 | 0 | 37.5 |
| 35 | 2-Hydroxymethyl-piperidine | 4 | ½ | 9.1/7.2 | 80 | 52.6 | 0 | 27.4 |
| 36 | 2-(B-Hydroxyethyl)-piperidine | 4 | ½ | 9.2/6.2 | 79.5 | 50.8 | 0 | 28.7 |
| 37 | N-(B-Hydroxyethyl)-piperazine | 4 | ½ | 8.4/5.2 | 75 | 23.5 | 0 | 51.5 |
| 38 | N-(B-Aminoethyl)-piperazine | 4 | ½ | 9.2/5.0 | 88.1 | 42.5 | 17.9 | 27.7 |

EXAMPLE 39

Into a first flask there were added;
0.38 grams (2 mmols) of cobaltous acetate Co-(OAc)₂.H₂O,
0.24 grams (4 mmols) of ethanolamine,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 175 grams of deionized water and 48.8 grams (400 mmols) of 2,6-xylenol.

To the resulting slurry which was stirred using a Labline cruciform stainless steel impeller turning at about 6,000 rpm there was added the stirred cobalt amine complex solution prepared above. The resulting mixture was stirred for 15 minutes after which 0.672 gms of sodium bicarbonate (as 8 ml of 1.0 N) solution was added. At this point the pH of the mixture was found to be 8.4. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase, washed once with 200 ml with water. The water phase had a pH of 8.9. A sample of the solid was removed, dissolved in acetone and analyzed by gas-liquid chromatography.

The solid product was then washed with xylene to remove oligomer and dried at 60° C. overnight. The product contained no diphenoquinone and 99+% tetramethylbiphenol as determined by spectrophotometric analysis.

EXAMPLE 40

Into a first flask there were added;
1.5 mmols of ferric formate,
4.5 mmols of ethanolamine,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; 175 grams of deionized water and 48.8 grams (400 mmols) of 2,6-xylenol.

To the resulting slurry which was stirred using a Labline cruciform stainless steel impeller turning at about 6,000 rpm there was added the stirred iron amine complex solution prepared above. The resulting mixture was stirred for 15 minutes after which 0.672 gms of sodium bicarbonate (as a 8 ml of 1.0 N) solution was added. At this point the pH of the mixture was found to be 8.8. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase washed once with 200 ml with water. The water phase had a pH of 8.5. A sample of the solid was removed, dissolved in acetone and analyzed by gas-liquid chromatography. The analysis indicated that 28 mol percent of the xylenol was unreacted. The solid product was then washed with xylene to remove oligomer and dried at 60° C. overnight. The product contained no diphenoquinone and 99.+% tetramethylbiphenol as determined by spectrophotometric analysis.

EXAMPLE 41

Into a first flask there were added;
2 mmols of manganous acetate Mn(OAc)$_2$.H$_2$O,
4 mmols of ethanolamine,
25 grams of ion exchanged water.

Into a 500 ml creased Morton flask fitted with a gas addition tube, a condenser, a thermometer, and a stirrer capable of operating at speeds in the range of from about 3,000 to about 10,000 rpm there were added; 10 gm of sodium lauryl sulfate, 150 grams of deionized water and 48.8 grams (400 mmols) of 2,6-xylenol.

To the resulting slurry which was stirred using a Labline cruciform stainless steel impeller turning at about 6,000 rpm there was added the stirred manganese amine complex solution prepared above. The resulting mixture was stirred and heated to 80°, then 12 meg sodium carbonate (as 12 ml of 1.0 N solution) was added slowly to achieve a control pH of 9.0. Oxygen was turned on, and the mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours. Base was added as required to maintain the control pH.

PRODUCT ISOLATION

The reaction slurry is cooled to room temperature and stirred with HCl is added to obtain the pH at 3–4. The slurry is filtered to remove the water phase, and washed with water until the filtrate is neutral. A sample of the solid was removed, dissolved in acetone and analyzed by gas-liquid chromatography. The analysis indicated that 25 mol percent of the 2,6-xylenol was unreacted.

The solid product was then washed with toluene to remove oligomer and dried at 60° C. overnight. The product contained 0.52% of diphenoquinone and 99.48% of tetramethylbiphenol as determined by spectrophotometric analysis

EXAMPLE 42

Into a first flask there were added;
0.4 grams (2 mmols) of cupric acetate Cu(OAc)$_2$.H$_2$O,
0.24 grams (4 mmols) of ethanolamine,
25 grams of ion exchanged water.

Into a 500 ml creased Morton flask, fitted with a gas addition tube, a condenser, a thermometer, and a stirrer capable of operating at speeds in the range of from about 3,000 to about 10,000 rpm there were added; .2 gm of sodium lauryl sulfate, 175 grams of deionized water and 82.4 grams (400 mmols) of 2,6-di-t-butyl phenol.

To the resulting slurry which was stirred using a Labline cruciform stainless steel impeller turning at about 6,000 rpm there was added the stirred copper amine complex solution prepared above. The resulting mixture was stirred for 15 minutes after which 1.680 gms of sodium bicarbonate (as a 20 ml of 1.0 N) solution was added over a period of 3 minutes. At this point the pH of the mixture was found to be 8.9. The sample was returned to the reactor which was then heated to 80° C. The mixture was stirred under oxygen. The oxygen flow was rapid at the beginning to flush the system. After about ½ hour, oxygen flow was reduced and maintained at a level sufficient to cause slow bubbling in a bubbler attached to the top of the condenser. The temperature was controlled by a Therm-O-Watch. The reaction mixture was stirred vigorously and maintained under oxygen for the prescribed reaction time of 6 hours.

PRODUCT ISOLATION

The reaction slurry was cooled to room temperature and filtered to remove the water phase washed once with 200 ml with water. The water phase had a pH of 8.3. A sample of the solid was removed, dissolved in acetone and analyzed by gas-liquid chromatography. The analysis indicated the 99.+% mol percent of the 2,6-di-t-butyl phenol had reacted.

The solid product was then washed with xylene to remove oligomer and dried at 60° C. overnight. The product contained 99.+% diquinone as determined by spectrophotometric analysis.

The following Table VI shows the results of Examples 42-49. The Examples except Example 46 were prepared according to the procedure of Example 42 with varying only in the selection of starting phenol. Example 46 was not subjected to a xylene wash but was instead triturated with ethanol followed by filtration.

TABLE VI

| Example | Phenol | Mmoles | pHo/pHf | Of Phenol | Oligo | to: DQ | Biphenol |
|---|---|---|---|---|---|---|---|
| 42 | 2,6-Di-t-butyl | 400 | 8.9/8.3 | 99+ | — | 99+ | — |
| 43 | 2,6-Di-sec-butyl | 200 | 8.8/9.4 | 99+ | — | 14 | 56 |
| 44 | 2,6-Xylenol | 400 | 8.6/8.0 | 92 | 12.1 | — | 80 |
| 45 | 2,6-Dimethoxy | 400 | 8.4/7.6 | 99 | 6 | 93.3 | — |
| 46 | 2,4-Di-t-butyl | 400 | 8.6/9.0 | 99 | — | — | >66.3 |
| 47 | 1-naphthol | 300 | 8.5/8.2 | 99 | 3 | 96 | — |
| 48 | 2-Me-4-t-butyl | 400 | 8.4/8.9 | 90 | — | — | >35 |
| 49 | 2-Me-6-t-butyl | 400 | 8.5/— | 99 | — | 75.4[5] | — |

(Mole & Conversion)

What is claimed is:

1. A method of preparing a carbon-carbon coupled condensation product of an "alkylphenol", an "alkoxyphenol" or a "1-naphthol" having one of the following formulas I-V:

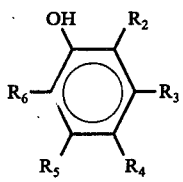

I.

wherein $R_2$ and $R_6$ are alkyl groups, $R_3$ and $R_5$ are hydrogen or alkyl groups and $R_4$ is hydrogen or methyl, provided that $R_3$ and $R_5$ are not simultaneously tertiary alkyl, said alkyl groups having 1-12 carbon atoms,

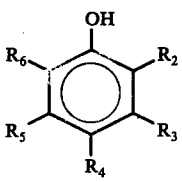

II.

wherein $R_2$ and $R_4$ are alkyl groups, $R_3$ and $R_5$ are hydrogen or alkyl groups and $R_6$ is hydrogen, provided that at least one of $R_2$ and $R_4$ is a tertiary alkyl group, said alkyl groups having 1-12 carbon atoms,

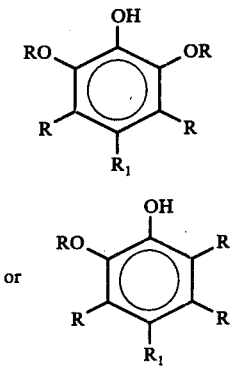

III.

wherein each R is an alkyl group having 1-12 carbon atoms or alkoxy group having 1-6 carbon atoms and $R_1$ is hydrogen or methyl, provided that both substituents adjacent to $R_1$ are not simultaneously tertiary alkyl or tertiary alkoxy,

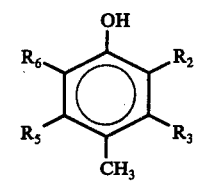

IV.

wherein $R_2$, $R_3$ and $R_4$ are hydrogen, alkyl groups containing from 1 to 5 carbon atoms or alkoxy groups containing 1-6 carbon atoms provided that at least one of $R_2$ and $R_4$ is hydrogen and $R_5$, $R_6$, $R_7$ and $R_8$ are hydrogen, alkyl groups having 1-5 carbon atoms or alkoxy groups having 1-6 carbon atoms, provided that tertiary alkyl or tertiary alkoxy groups are not attached to adjacent carbon atoms of the naphthalene molecule, or

V.

wherein $R_3$ is hydrogen, an alkyl group having 1-12 carbon atoms or an alkoxy group having 1-6 carbon atoms, $R_5$ is a primary or secondary alkyl group having 1-5 carbon atoms and $R_2$ and $R_6$ are alkyl groups having 1-12 carbon atoms or alkoxy groups having 1-6 carbon atoms, by an oxidative coupling reaction said method comprising contacting an aqueous mixture of the phenol or naphthol with oxygen or oxygen containing gas in the presence of a catalyst system consisting essentially of a cupric, manganous, cobaltous, or ferric metal complex of an amine selected from the class consisting of:
an "aliphatic hydroxy amine",
a heterocyclic hydroxy amine, and
an "aliphatic diamine"
and a sufficient amount of an alkaline material selected from the group consisting of alkali metal hydroxides, alkali metal carbonates and alkali metal bicarbonates to maintain the pH in a range of about 5-10 during the oxidative coupling reaction.

2. A method, as claimed in claim 1, wherein the aqueous phenol mixture additionally comprises a surfactant.

3. A method, as claimed in claim 2, wherein the metal complex and surfactant are a single compound.

4. A method, as claimed in claim 2, wherein the surfactant is sodium lauryl sulfate and is present in an amount equal to at least 0.0005 mols per mol of phenol or naphthol.

5. A method, as claimed in claim 1, wherein the phenol is an alkylphenol.

6. A method, as claimed in claim 5, wherein the alkylphenol is a 2,6-dialkylphenol.

7. A method, as claimed in claim 6, wherein the alkylphenol is 2,6-xylenol.

8. A method, as claimed in claim 5, wherein the alkyl groups of said alkylphenol contain from 1 to about 5 carbon atoms.

9. A method, as claimed in claim 1, wherein the catalyst system comprises a cupric amine complex.

10. A method, as claimed in claim 9 wherein the alkylphenol is 2,6-xylenol.

11. A method, as claimed in claim 9, wherein the cupric amine complex is prepared from cupric acetate and ethanolamine.

12. A method, as claimed in claim 1, wherein the amount of metal complex is equal to at least about 0.2 mmols per mol of phenol or naphthol.

13. A method, as claimed in claim 1, wherein the alkaline material is an alkali metal bicarbonate.

14. A method, as claimed in claim 13, wherein the alkali metal bicarbonate is sodium bicarbonate.

15. A method, as claimed in claim 1, wherein the amount of alkaline material is equal to at least about 3 mmols per mol of phenol or naphthol.

16. A method, as claimed in claim 1, wherein the phenol is an alkylphenol having the following formula:

$$\begin{array}{c} OH \\ R_6 \underset{R_5}{\overset{}{\bigcirc}} R_2 \\ R_4 \end{array}$$

wherein $R_2$ and $R_6$ are alkyl and $R_3$ and $R_5$ are hydrogen or alkyl and $R_4$ is hydrogen or methyl provided that $R_3$ and $R_5$ are not simultaneously tertiary alkyl.

17. A method, as claimed in claim 16, wherein the alkyl phenol is 2,4,6-trimethylphenol.

* * * * *